(12) United States Patent
Netzel

(10) Patent No.: US 11,672,590 B2
(45) Date of Patent: Jun. 13, 2023

(54) SLIP-RING CONTACT ASSEMBLY FOR ELECTROSURGICAL INSTRUMENTS

(71) Applicant: Covidien LP, Mansfield, MA (US)

(72) Inventor: Ken Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 398 days.

(21) Appl. No.: 16/919,386

(22) Filed: Jul. 2, 2020

(65) Prior Publication Data
US 2022/0000538 A1 Jan. 6, 2022

(51) Int. Cl.
A61B 18/14 (2006.01)
H01R 39/08 (2006.01)
A61B 18/00 (2006.01)

(52) U.S. Cl.
CPC ............. *A61B 18/14* (2013.01); *H01R 39/08* (2013.01); *A61B 18/1442* (2013.01); *A61B 2018/00083* (2013.01); *A61B 2018/00178* (2013.01); *H01R 2201/12* (2013.01)

(58) Field of Classification Search
CPC ......... A61B 18/08; A61B 18/12; A61B 18/14; A61B 18/1442; A61B 2017/00411; A61B 2017/00477; A61B 2018/00083; A61B 2018/00178; A61B 2018/00202; A61B 2018/0091; H01R 2201/12; H01R 39/08; H01R 39/64
USPC .......................................................... 606/51
See application file for complete search history.

(56) References Cited

U.S. PATENT DOCUMENTS

| | | |
|---|---|---|
| 7,131,844 B1 | 11/2006 | Wurr |
| 7,560,847 B2 | 7/2009 | Hsu |
| 7,632,270 B2 * | 12/2009 | Livneh ............... A61B 18/1445 606/205 |
| 8,012,154 B2 * | 9/2011 | Livneh ............... A61B 18/1445 606/51 |
| 8,206,307 B2 | 6/2012 | Barnard et al. |
| 8,403,856 B2 | 3/2013 | Corl |
| 8,531,064 B2 | 9/2013 | Robertson et al. |
| 9,065,232 B2 | 6/2015 | Li et al. |
| 9,101,385 B2 | 8/2015 | Shelton, IV et al. |

(Continued)

FOREIGN PATENT DOCUMENTS

WO 2018217596 A2 11/2018

OTHER PUBLICATIONS

Extended European Search Report dated Nov. 22, 2021 issued in corresponding EP Appln. No. 21183470.0.

*Primary Examiner* — Michael F Peffley
(74) *Attorney, Agent, or Firm* — Carter, DeLuca & Farrell LLP

(57) ABSTRACT

A surgical instrument includes a slip-ring contact assembly. The slip-ring contact assembly includes an insulative housing defining a plurality of slots. A plurality of slip-ring contacts is operably supported in the insulative housing. Each slip-ring contact is configured to engage one or more electrical contacts formed circumferentially around a rotatable shaft of the surgical instrument. Each slip-ring contact includes a tang extending through a corresponding slot defined in the insulative housing and configured to be operably connected to an external wire connection. The plurality of slip-ring contacts is configured to allow unlimited rotation of the rotatable shaft while maintaining continuous electrical contact between each slip-ring contact and the corresponding electrical contact of the rotatable shaft.

14 Claims, 5 Drawing Sheets

(56) References Cited

U.S. PATENT DOCUMENTS

| | | | |
|---|---|---|---|
| 9,579,080 B2 | 2/2017 | Fearnot et al. | |
| 9,608,395 B2 | 3/2017 | Overweg | |
| 9,627,831 B1 | 4/2017 | Wagman et al. | |
| 9,968,343 B2 | 5/2018 | Jeong et al. | |
| 10,039,595 B2* | 8/2018 | Sakaguchi | A61B 18/1445 |
| 10,211,586 B2 | 2/2019 | Adams et al. | |
| 10,389,074 B2 | 8/2019 | Binder et al. | |
| 10,631,861 B2 | 4/2020 | Shelton, IV et al. | |
| 11,426,230 B2* | 8/2022 | Ding | A61B 17/295 |
| 2005/0165443 A1 | 7/2005 | Livneh | |
| 2013/0274732 A1 | 10/2013 | Wiener et al. | |
| 2015/0133928 A1* | 5/2015 | Soni | A61B 18/1445 |
| | | | 606/51 |
| 2016/0121143 A1 | 5/2016 | Mumaw et al. | |
| 2019/0290273 A1* | 9/2019 | Shelton, IV | A61B 17/320092 |
| 2020/0197075 A1* | 6/2020 | Hammerland | A61B 18/1445 |

* cited by examiner

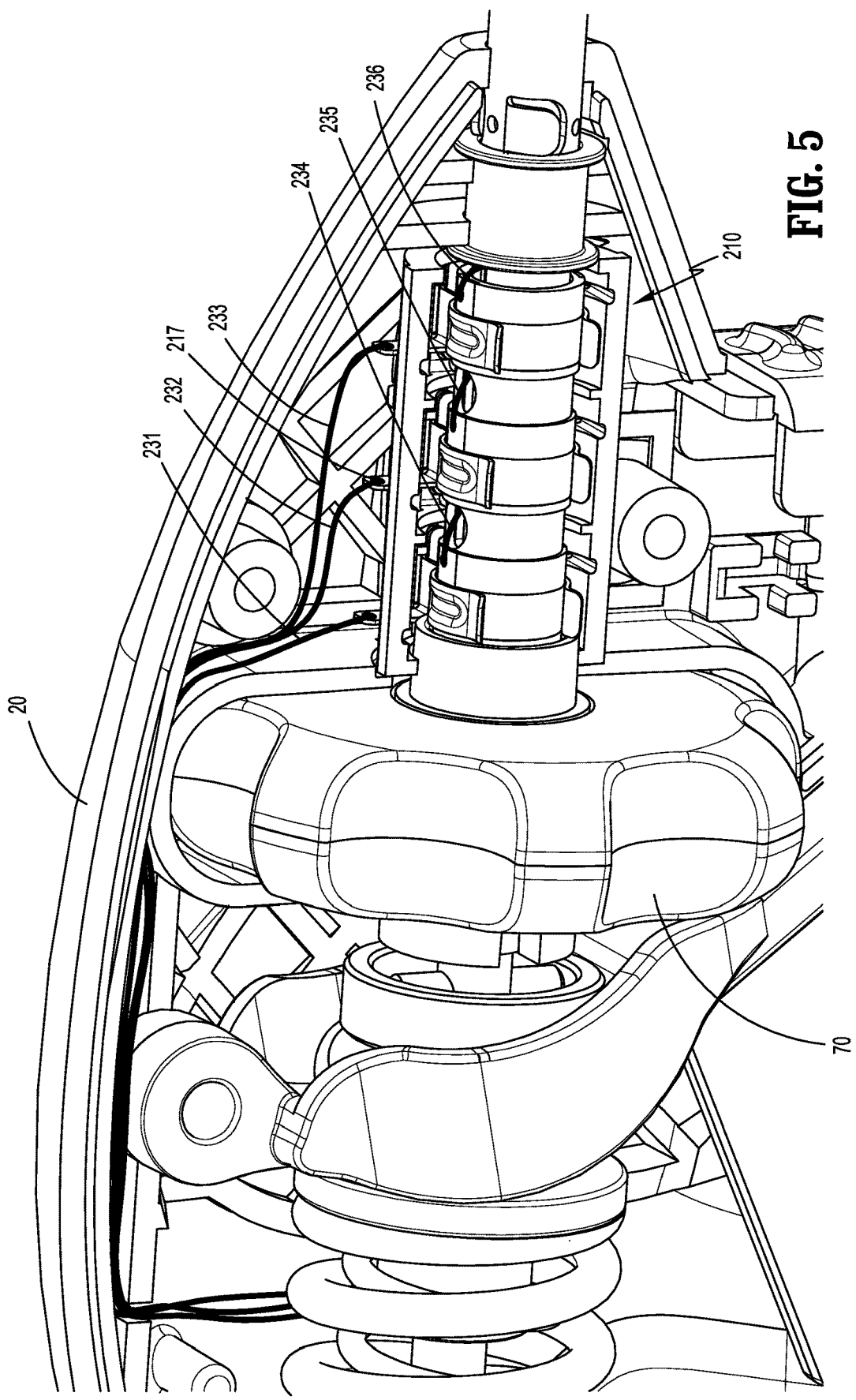

SLIP-RING CONTACT ASSEMBLY FOR ELECTROSURGICAL INSTRUMENTS

FIELD

The present disclosure relates to surgical instruments and, more particularly, to a slip-ring contact assembly for electrosurgical instruments.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

Provided in accordance with aspects of the present disclosure is a surgical instrument including a handle assembly including a housing and a rotating assembly operably coupled to the housing. A rotatable shaft extends distally from the housing and is rotatable upon actuation of the rotating assembly. The rotatable shaft defines a proximal portion operably coupled to the housing. The rotatable shaft includes a plurality of electrical contacts formed circumferentially around and spaced along the proximal portion of the rotatable shaft. An end effector is supported at a distal portion of the rotatable shaft. A slip-ring contact assembly is operably supported in the housing. The slip-ring contact assembly includes an insulative housing defining a plurality of slots. A plurality of slip-ring contacts is operably supported in the insulative housing. Each slip-ring contact is operably engageable about a corresponding one of the electrical contacts of the proximal portion of the rotatable shaft. Each slip-ring contact includes a tang extending through a corresponding slot defined in the insulative housing and operably connected to an external wire connection. The slip-ring contacts allow unlimited rotation of the rotatable shaft while maintaining continuous electrical contact between each slip-ring contact and the corresponding electrical contact of the proximal portion of the rotatable shaft.

In some aspects of the disclosure, the slip-ring contact assembly further includes one or more walls electrically isolating a first slip-ring-contact from a second slip-ring contact.

In some aspects of the disclosure, one or more of the electrical contacts operably engaged about the proximal portion of the rotatable shaft includes an internal wire connection extending along a longitudinal axis of the rotatable shaft. One or more internal wires connect the internal wire connection to the rotatable shaft.

In some aspects of the disclosure, each slip-ring contact includes a first curved arm and a second curved arm. The first curved arm and the second curved arm define an opening configured to receive the proximal portion of the rotatable shaft to rotatably secure the rotatable shaft to the slip-ring contacts In some aspects of the disclosure, the slip-ring contacts are adapted to electrically connect to a source of electrosurgical energy to deliver electrosurgical energy to the end effector.

In some aspects of the disclosure, a collar is disposed about the proximal portion of rotatable shaft. The electrical contacts operably engaged about the proximal portion of the rotatable shaft are formed on the collar.

In some aspects of the disclosure, rotation of the rotatable shaft by the rotating assembly correspondingly rotates the end effector.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 5 is an internal perspective view of the wiring of the slip-ring contact assembly of FIG. 2.

DETAILED DESCRIPTION

Figure 1:
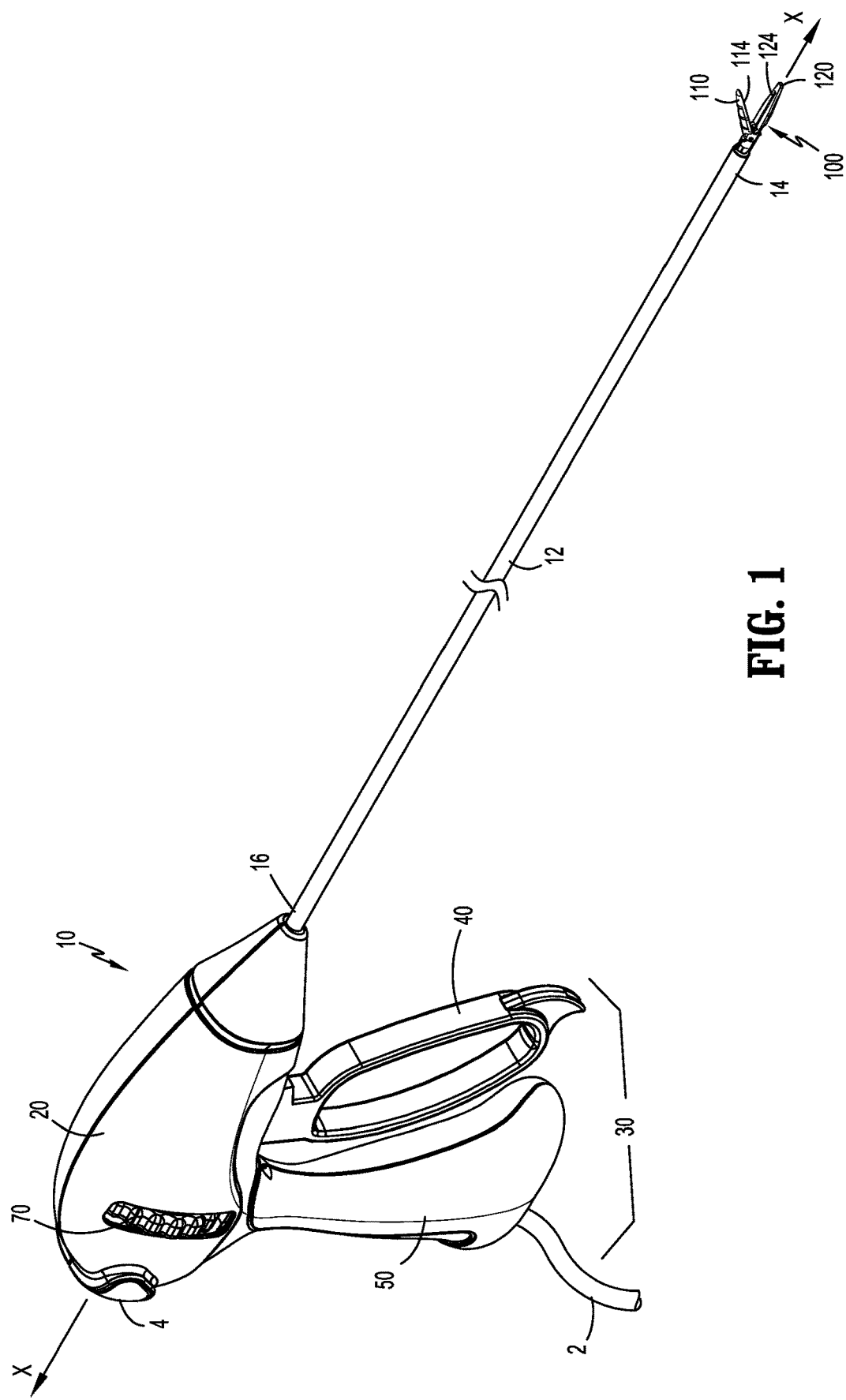
FIG. 1 is a perspective view of an endoscopic surgical forceps for use in accordance with the aspects and features of the disclosure.
Figure 2:
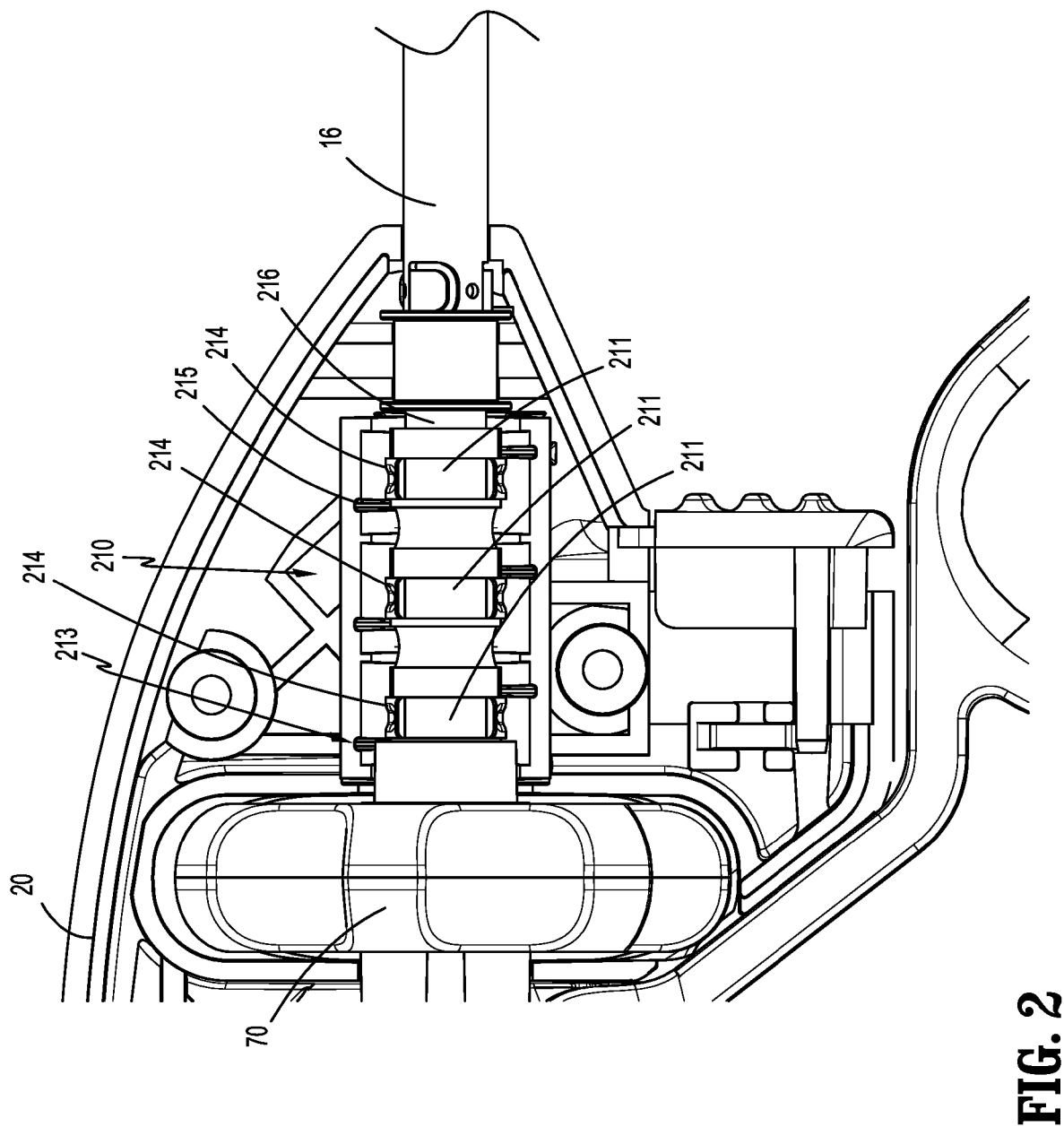
FIG. 2 is a cross-sectional view of a handle assembly housing and a proximal portion of a rotatable shaft disposed in a slip-ring contact assembly of the endoscopic surgical forceps of FIG. 1.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Referring to FIG. 1, an embodiment of a surgical instrument, such as a surgical forceps, provided in accordance with the present disclosure is shown generally identified by reference numeral 10.

Forceps 10 generally includes a housing 20, a handle assembly 30, handle 50, trigger 40, a rotating assembly 70, an activation switch 4, and an end effector assembly 100. Forceps 10 further includes a shaft 12 having a distal end 14 configured to engage end effector assembly 100 and a proximal end 16 that engages housing 20. The shaft 12 is rotatable, as described below in more detail, and includes a proximal portion 216 operably coupled to the housing 20. The terms "shaft" and "rotatable shaft" may be used interchangeably herein.

Forceps 10 also includes cable 2 that connects forceps 10 to an energy source (not shown), e.g., a generator or other suitable power source, although forceps 10 may alternatively be configured as a battery-powered device. Cable 2 is in electrical communication with at least one wire that has sufficient length to extend through shaft 12 in order to provide energy to one or both tissue-treating surfaces 114, 124 of jaw members 110, 120, respectively. Other electrical configurations are envisioned to provide electrical energy to the jaw members 114, 124, e.g., conductive tubes, etc. Activation switch 4 is electrically coupled to tissue-treating surfaces 114, 124 of jaw members 110, 120, respectively, and the source of energy for enabling the selective supply of energy to jaw members 110, 120 for treating tissue grasped therebetween. Rotating assembly 70 is rotatable in either direction to ultimately rotate end effector assembly 100 relative to housing 20.

Referring to FIGS. 1 to 5, the surgical instrument 10 includes the handle assembly 30 and the rotating assembly 70 both operably coupled to the housing 20. The rotatable shaft 12 extends distally from the housing 20 and is rotatable upon actuation of the rotating assembly 70.

The rotatable shaft 12 defines the proximal portion 216 operably coupled to the housing 20. The rotatable shaft 12 includes a plurality of electrical contacts 211 formed circumferentially around and spaced along the proximal portion 216 of the rotatable shaft 12 (e.g., spaced along a longitudinal axis X-X identified in FIG. 1). End effector 100 is supported at the distal portion 14 of the rotatable shaft 12. Rotation of the rotating assembly 70 correspondingly rotates the rotatable shaft 12 and also correspondingly rotates the end effector 100.

A slip-ring contact assembly 210 is operably supported in the housing 20. The slip-ring contact assembly 210 includes an insulative housing 212 defining a plurality of slots 213. A plurality of slip-ring contacts 214 is operably supported in the insulative housing 212. Each slip-ring contact 214 is operably engageable about a corresponding one of the electrical contacts 211 of the proximal portion 216 of the rotatable shaft 12. The slip-ring contacts 214 are adapted to electrically connect to a source of electrosurgical energy (e.g., via cable 2 shown in FIG. 1) to deliver electrosurgical energy to the end effector 100. Each slip-ring contact 214 includes a tang 215 extending through a corresponding slot 213 defined in the insulative housing 212 and operably connected to an external wire connection 217. Each tang 215 may include its own external wire connection 217 respectively connected to at least one wire (e.g., one of wires 231, 232 or 233 shown in FIG. 5) to supply electrosurgical energy to the tang 215, which is, in turn, in electrical communication with wiring extending through the rotatable shaft 12 along to the end effector 100 to supply electrosurgical energy to the tissue treating surfaces 114, 124 of the end effector 100.

At least one of the electrical contacts 211 operably engaged about the proximal portion 216 of the rotatable shaft 12 includes an internal wire connection 219 extending along the longitudinal axis (see, e.g., longitudinal axis X-X in FIG. 1) of the rotatable shaft 12. Each electrical contact 211 may respectively include its own internal wire connection 219, which is, in turn, connected with a corresponding wire (e.g., one of wires 234, 235 or 236 shown in FIG. 5) to connect the internal wire connection 219 with wiring extending through the rotatable shaft 12 to the end effector 100. The wires 234, 235 or 236 may each pass through an aperture (e.g., one of apertures 237, 238 or 239 shown in FIG. 4) that is in communication with wiring extending through an interior of the rotatable shaft 12, respectively.

The internal wire connections 219 extending along the longitudinal axis X-X are not covered by the slip-ring contacts 214, and thus the internal wire connections 219 remain internally exposed within the housing 20 (see, e.g., FIG. 5).

The slip-ring contacts 214 allow unlimited rotation of the rotatable shaft 12 while maintaining continuous electrical contact between each slip-ring contact 214 and the corresponding electrical contact 211 of the proximal portion 216 of the rotatable shaft 12. That is, the rotatable shaft 12 can be rotated, while correspondingly rotating end effector 100 in excess of 360 degrees without disrupting electrical contact between each slip-ring contact 214 and the corresponding electrical contact 211 of the proximal portion 216 of the rotatable shaft 12.

The slip-ring contact assembly 210 can be "snapped on" to the proximal portion 216 of the rotatable shaft 12 during assembly or manufacturing before external wiring (e.g., to external wirings 231, 232 or 233) is attached because tangs 215 allow wiring connections to be made after coupling the slip-ring contact assembly 210 to the proximal portion 216 of the rotatable shaft 12. This reduces manufacturing costs and decreases manufacturing time. The multiple external connections via tangs 215 also allow multiple electrical connections to the end effector 100 through the rotatable shaft 12.

Figure 3:
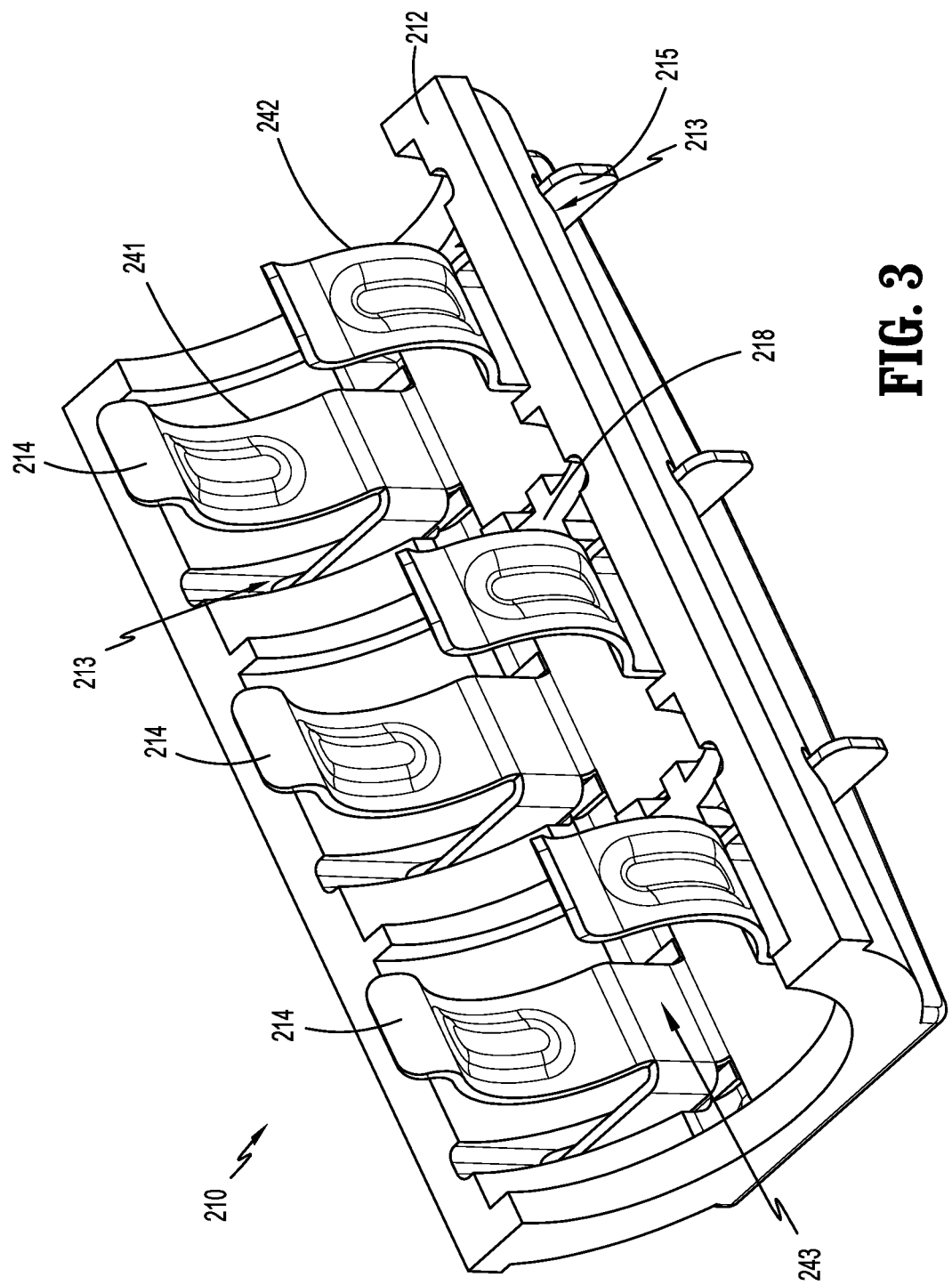
FIG. 3 is an enlarged, perspective view of the slip-ring contact assembly of FIG. 2.
Figure 4:
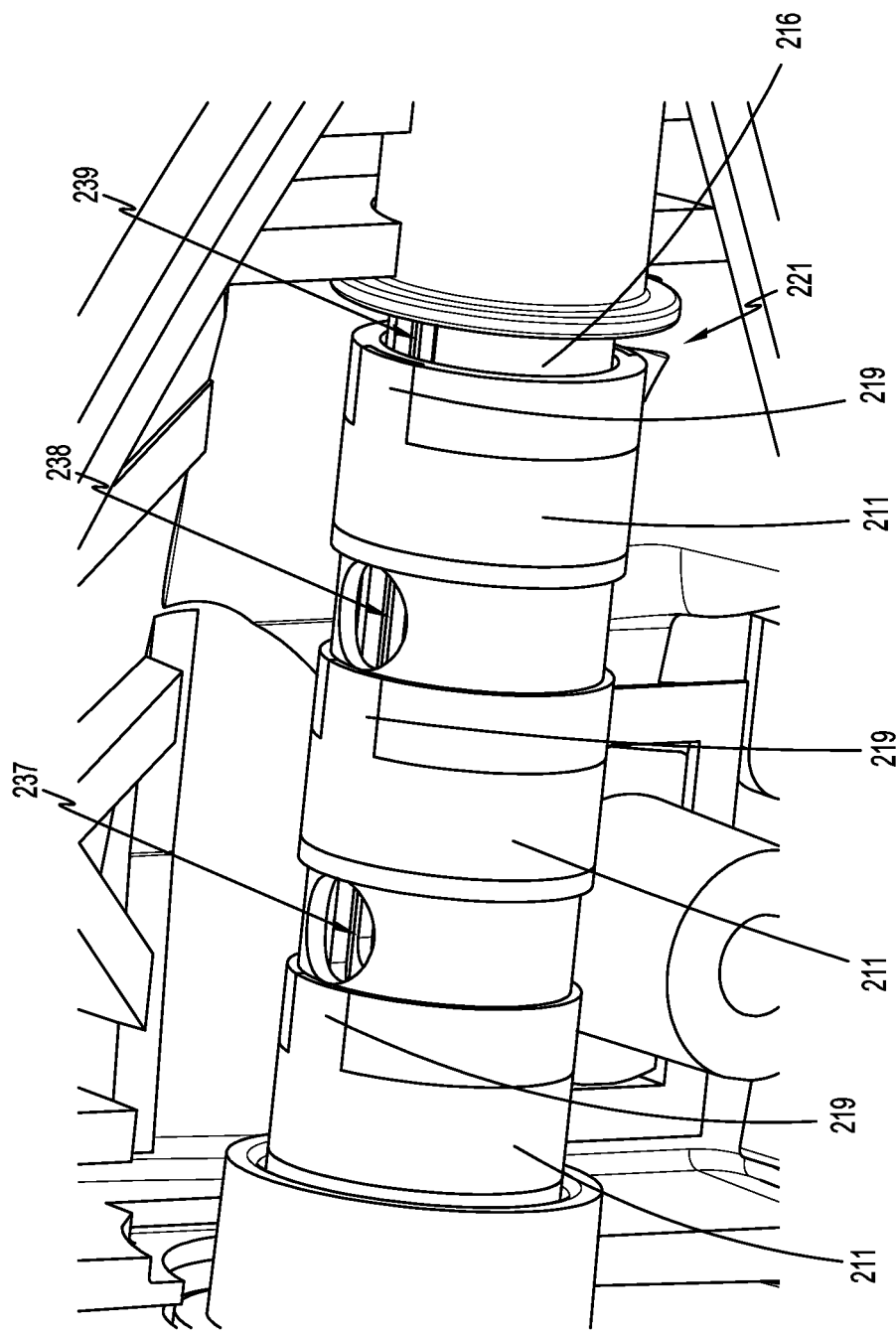
FIG. 4 is an enlarged, perspective view of the proximal portion of the rotatable shaft of FIG. 2.

The slip-ring contact assembly 210 further includes one or more walls 218 electrically isolating a first slip-ring-contact from a second slip-ring contact (see, e.g., FIG. 3). Each slip-ring contact 214 includes a first curved arm 241 and a second curved arm 242. Each slip ring contact 214 may be spaced apart from and electrically isolated from any adjacent slip ring contacts 214 by a respective wall 218. The first curved arms 241 and the second curved arms 242 define an opening 243 configured to receive the proximal portion 216 of the rotatable shaft 12 to rotatably secure the rotatable shaft 12 to the slip-ring contacts 214 of the slip ring contact assembly 210. Thus, the slip rings contacts 214 are spaced apart from each other along the longitudinal axis X-X (see, e.g., FIG. 1) and are respectively electrically isolated from each other by the walls 218.

A collar 221 may be operably coupled to the proximal portion 216 of the rotatable shaft 12 such that the collar 221 and the rotatable shaft 12 rotate in unison. The electrical contacts 211 may be formed circumferentially around the collar 221.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a handle assembly including a housing and a rotating assembly operably coupled to the housing;
   a rotatable shaft extending distally from the housing and rotatable upon actuation of the rotating assembly, the rotatable shaft defining a proximal portion operably coupled to the housing, the rotatable shaft including a plurality of electrical contacts formed circumferentially around and spaced along the proximal portion of the rotatable shaft;
   an end effector supported at a distal portion of the rotatable shaft; and
   a slip-ring contact assembly operably supported in the housing, the slip-ring contact assembly including:
     an insulative housing defining a plurality of slots; and
     a plurality of slip-ring contacts operably supported in the insulative housing, each slip-ring contact operably engageable about a corresponding one of the plurality of electrical contacts of the proximal portion of the rotatable shaft, each slip-ring contact including a tang extending through a corresponding slot defined in the insulative housing and operably connected to an external wire connection,
     wherein the plurality of slip-ring contacts allows unlimited rotation of the rotatable shaft while maintaining continuous electrical contact between each slip-ring contact and the corresponding electrical contact of the proximal portion of the rotatable shaft, and
     wherein each slip-ring contact of the plurality of slip ring contacts includes a first curved arm and a second curved arm defining an opening therebetween configured to operably receive a corresponding portion of the rotatable shaft therebetween in a snap-fit manner upon assembly thereof and in registration with a corresponding one of the plurality of electrical contacts of the proximal portion of the rotatable shaft.

2. The surgical instrument of claim 1, wherein the slip-ring contact assembly further includes at least one wall electrically isolating a first slip-ring-contact of the plurality of slip-ring contacts from a second slip-ring contact of the plurality of slip ring contacts.

3. The surgical instrument of claim 1, wherein at least one of the electrical contacts operably engaged about the proximal portion of the rotatable shaft includes an internal wire connection extending along a longitudinal axis of the rotatable shaft.

4. The surgical instrument of claim 3, further including at least one internal wire connecting the internal wire connection to the rotatable shaft.

5. The surgical instrument of claim 1, wherein the plurality of slip-ring contacts is adapted to electrically connect to a source of electrosurgical energy to deliver electrosurgical energy to the end effector.

6. The surgical instrument of claim 1, further including a collar disposed about the proximal portion of rotatable shaft and wherein the plurality of electrical contacts operably engaged about the proximal portion of the rotatable shaft are formed on the collar.

7. The surgical instrument of claim 1, wherein rotation of the rotatable shaft by the rotating assembly correspondingly rotates the end effector.

8. A surgical instrument, comprising:
   a handle assembly including a housing and a rotating assembly operably coupled to the housing;
   a rotatable shaft extending distally from the housing and rotatable upon actuation of the rotating assembly, the rotatable shaft defining a proximal portion operably coupled to the housing, a collar disposed about and operably engaged with the proximal portion of the rotatable shaft;
   a plurality of electrical contacts formed circumferentially around and spaced along the collar;
   an end effector supported at a distal portion of the rotatable shaft, wherein rotation of the rotatable shaft by the rotating assembly correspondingly rotates the end effector; and
   a slip-ring contact assembly operably supported in the housing, the slip-ring contact assembly including:
     an insulative housing defining a plurality of slots; and
     a plurality of slip-ring contacts operably supported in the insulative housing, each slip-ring contact operably engageable about a corresponding one of the plurality of electrical contacts of the collar, each slip-ring contact including a tang extending through a corresponding slot defined in the insulative housing and operably connected to an external wire connection,
     wherein the plurality of slip-ring contacts allows unlimited rotation of the rotatable shaft while maintaining continuous electrical contact between each slip-ring contact and the corresponding electrical contact of the collar,
     wherein each slip-ring contact of the plurality of slip ring contacts includes a first curved arm and a second curved arm defining an opening therebetween configured to operably receive a corresponding portion of the rotatable shaft therebetween in a snap-fit manner upon assembly thereof and in registration with a corresponding one of the plurality of electrical contacts of the proximal portion of the rotatable shaft.

9. The surgical instrument of claim 8, wherein the slip-ring contact assembly further includes at least one wall electrically isolating a first slip-ring-contact of the plurality of slip-ring contacts from a second slip-ring contact of the plurality of slip ring contacts.

10. The surgical instrument of claim 8, wherein the plurality of slip-ring contacts is adapted to electrically connect to a source of electrosurgical energy to deliver electrosurgical energy to the end effector.

11. The surgical instrument of claim 8, wherein at least one of the electrical contacts operably engaged about the proximal portion of the rotatable shaft includes an internal wire connection extending along a longitudinal axis of the rotatable shaft.

12. A slip-ring contact assembly, comprising:
    an insulative housing defining a plurality of slots; and a plurality of slip-ring contacts operably supported in the insulative housing, each slip-ring contact configured to engage at least one electrical contact formed circumferentially around a rotatable shaft of a surgical instrument, each slip-ring contact including a tang extending through a corresponding slot defined in the insulative housing and configured to be operably connected to an external wire connection, wherein the plurality of slip-ring contacts is configured to allow unlimited rotation of the rotatable shaft while maintaining continuous electrical contact between each slip-ring contact and the corresponding electrical contact of the rotatable shaft, wherein each slip-ring contact of the plurality of slip ring contacts includes a first curved arm and a second curved arm defining an opening therebetween configured to operably receive a corresponding portion of the rotatable shaft therebetween in a snap-fit manner upon assembly thereof and in registration with a corresponding one of the at least one electrical contacts of the rotatable shaft.

13. The slip-ring contact assembly of claim 12, wherein the slip-ring contact assembly further includes at least one wall electrically isolating a first slip-ring-contact of the plurality of slip-ring contacts from a second slip-ring contact of the plurality of slip ring contacts.

14. The slip-ring contact assembly of claim 12, wherein the plurality of slip-ring contacts is adapted to electrically connect to a source of electrosurgical energy to deliver electrosurgical energy to an end effector.

* * * * *